United States Patent [19]

Peekna

[11] 4,089,212
[45] May 16, 1978

[54] BRINELL SANDWICH TRANSDUCER

[75] Inventor: Andres Peekna, Vicksburg, Miss.

[73] Assignee: The United States of America as represented by the Secretary of the Army, Washington, D.C.

[21] Appl. No.: 777,383

[22] Filed: Mar. 14, 1977

[51] Int. Cl.$^2$ .......................... G01N 3/08; G01N 3/48
[52] U.S. Cl. ........................................ 73/94; 73/81; 73/88 E; 73/141 R; 116/114 AH; 177/2
[58] Field of Search ................ 73/81, 85, 88 E, 88 R, 73/94, 141 R; 116/114 AH; 177/2

[56] References Cited

U.S. PATENT DOCUMENTS

| 2,195,451 | 4/1940 | Edwards | 177/2 |
| 2,370,784 | 3/1945 | Edwards | 73/141 R X |
| 3,141,440 | 7/1964 | Platt | 116/141 AH |
| 3,178,935 | 4/1965 | McRitchie | 73/94 |
| 3,373,716 | 3/1968 | Williams | 116/114 AH |

Primary Examiner—Richard C. Queisser
Assistant Examiner—Charles Gorenstein
Attorney, Agent, or Firm—Thomas O. Maser

[57] ABSTRACT

The instant Brinell sandwich transducer has a layer of small hardened steel balls between two layers of softer materials. The balls may be closely packed or separated into a less dense array by a spacer. Indentations in the softer materials indicate the maximum compressive forces that have been applied to the balls. The diameters of identations in a sampling pattern are measured by a microscope since such diameters indicate the magnitude of the forces which have been registered by the transducer. Good resolution over a range of more than a factor of 100 has been obtained. With pulses ranging from static to approximately half-sines with rise times of 0.1 millisecond and a fall time of 0.1 millisecond, rate effects have been insignificant. That is, the indicated gauge pressure is not sensitive to the rate at which the pressure is applied for a broad range of pulse rise times and durations. Also, these gauges incorporate high axial stiffness and flat geometry.

7 Claims, 4 Drawing Figures

BRINELL SANDWICH TRANSDUCER

GOVERNMENT USE

This invention may be used by or for the government of United States of America for governmental purposes without the payment to me of any royalties thereon or therefor.

BACKGROUND OF THE DISCLOSURE

Edwards, U.S. Pat. No. 2,370,784, teaches the measurement of weight by the indentation by a solid ball resulting from the application of large static weights. McRitchie, U.S. Pat. No. 3,178,935, teaches the measurement of pressure by means of indentation by three ball members in a triangular configuration. The Brinell sandwich transducer of this invention provides for a structure which introduces a capability to measure large stresses in a variety of environments heretofore unprovided for. The instant transducer is not sensitive to the rate at which the pressure is applied for a broad range of pressure pulses. This transducer indicates the distribution of applied pressure. The structure of the transducer enables use in extreme soil conditions. None of these stated features is found in the prior art.

SUMMARY OF THE INVENTION

The Brinell sandwich transducer of this invention provides a rugged structure that can measure the stresses within an environment in which an explosion occurs. This transducer can withstand severe environmental conditions such as extremely high stress, high temperature, large deformation, and electromagnetic and nuclear radiation. The disc-shaped surfaces confine a plurality of ball members, with edge means completing the confinement. The material of the balls is harder than the material of the confining surfaces. The small hardened steel balls are harder than either of the two aluminum alloys 7075-T6 or 6061-T6 found to be satisfactory for this device. The choice of alloy depends to some extent upon desired range and stiffness, and on whether the slight sensitivity to application rate present in 6061-T6 is detrimental, or whether complete insensitivity to application rate is desired, requiring the 7075-T6 alloy. The decision on whether to spread the balls into a less dense array with a spacer depends on desired range and stiffness. The transducer structure is provided with sealing means and structural features that enable the transducer to withstand extreme pressure and environmental conditions. This gauge is capable of indicating the distribution of the pressures applied thereto by variations in the size of the indentations from various of the plurality of balls.

It is, therefore, an object of this invention to provide a Brinell sandwich transducer that measures compressive forces produced by very large, as well as smaller, explosions.

It is another object of this invention to provide a Brinell sandwich transducer that has good resolution over a wide range of compressive forces.

It is still another object of this invention to provide a Brinell sandwich transducer that is insensitive to rate effect of applied pressures.

It is yet another object of this invention to provide high axial stiffness and flat geometry which are desirable for stress measurement by a transducer in soil.

It is a further object of this invention to provide a Brinell sandwich transducer that indicates the distribution of the applied pressure.

It is a still further object of this invention to provide a Brinell sandwich transducer that is not destroyed by the testing condition.

It is yet a further object of this invention to provide a Brinell sandwich transducer that produces stress measurements in extreme environmental conditions.

These and other objects and advantages of the present invention will become apparent to those skilled in the art after having read the following detailed description of the preferred embodiments which are illustrated in the figures of the drawing in which:

DESCRIPTION OF A PREFERRED EMBODIMENT

Figure 1:
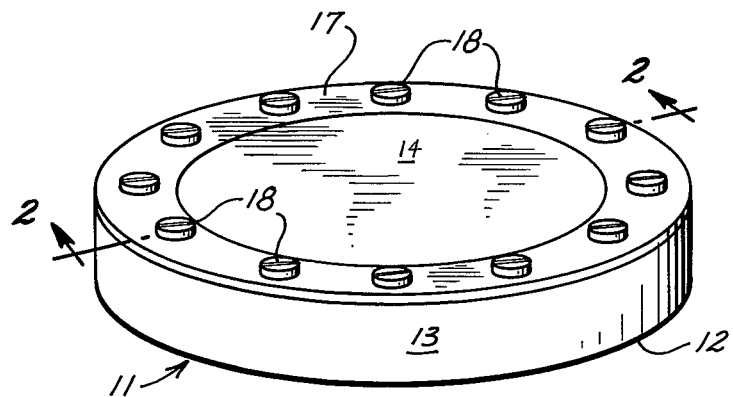
FIG. 1 is a pictorial representation of the device of the present invention.
Figure 2:
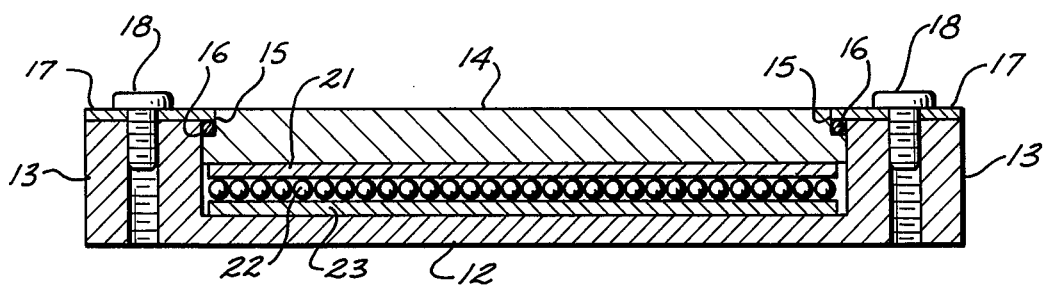
FIG. 2 is a cross sectional view of the structure of FIG. 1 as seen at 2—2.

Turning now to the drawings in which like numerals refer to like elements throughout the three figures, FIG. 1 shows the Brinell sandwich transducer 11 in pictorial form. A body member is configured as a disc-shaped bottom 12 with integral tubular thick side walls 13 defining a central chamber. A disc-shaped cover means 14, of material similar to the material of the body member, fits snugly within the side walls 13. As shown in FIG. 2, cover 14 is provided with an annular groove 15 at the top thereof for supporting an O-ring sealing member 16. A retaining ring 17 is dimensioned so that its outside diameter is substantially the same as the diameter of bottom 12 and its inner opening diameter is just slightly more than the diameter of top 14 minus the material removed therefrom by annular groove 15. Securing means 18, such as screws or bolts, are spaced around retaining ring 17 at intervals sufficient to properly seal the ring to the tubular sides 13 of bottom 12 while confining the O-ring member 16 within the annular groove 15 to establish a tight seal for top means 14. The top 14 and the retaining ring 17 form a substantially planar surface when the transducer is properly assembled.

Within top 14, bottom 12 and sides 13 are confined in tight association an upper low-strain-rate-sensitive material flat circular plate 21, a plurality of small hardened steel balls 22, and a lower low-strain-rate-sensitive material flat circular plate 23. The top means 14 is dimensioned so that when the securing means 18 are properly tightened, the retaining ring 17 places a slight compressive force on the upper and lower plates 21 and 23 and balls 22 so that the balls are snugly held. The O-ring 16 is, therefore, compressed and substantial planar relationship between the outer surface of top 14 and the retaining ring 17 is obtained.

Figure 3:
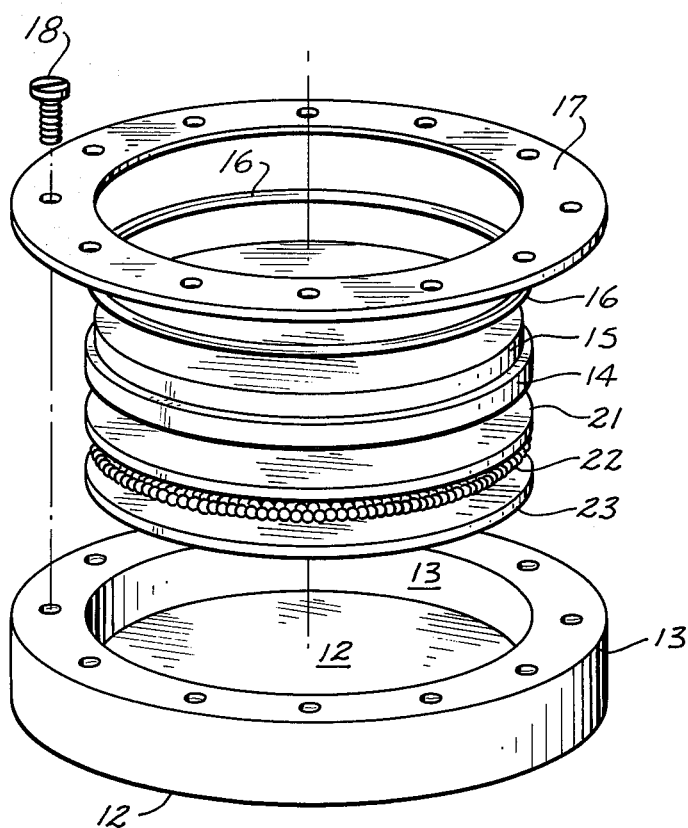
FIG. 3 is an exploded view of the individual elements in the device of the present invention.

FIG. 3 shows the several components of the Brinell sandwich in exploded view for better understanding of the relationship of the several components.

The materials chosen for the device are as follows. The plate 23 is made of aluminum alloy 7075-T6, the plate 21 of either aluminum alloy 6061-T6 or 7075-T6, the balls are of hardened steel, and the O-ring is of an elastomer such as Parker compound No. N674-70. The material for the body of the transducer is not as critical as the material of the plates, and since the density of aluminum is much closer to earth media densities than that of steel, the use of aluminum minimizes acceleration sensitivity. Aluminum alloy 7075-T651 is chosen for the body because of its high strength and stress-relieved temper. A coating, such as electroless nickel, is placed on the body to reduce the effect of alkaline environments on aluminum.

Aluminum alloy 7075-T6 contains 5.1 to 6.1 percent zinc, 2.1 to 2.9 percent manganese, 1.2 to 2.0 percent copper, 0.18 to 0.40 percent chronimum, and the remainder is aluminum. Aluminum alloy 6061-T6 contains 0.8 to 1.2 percent manganese, 0.4 to 0.8 percent silicon, 0.15 to 0.35 percent chronimum, 0.15 to 0.40 percent copper, and the remainder is aluminum.

Figure 4:
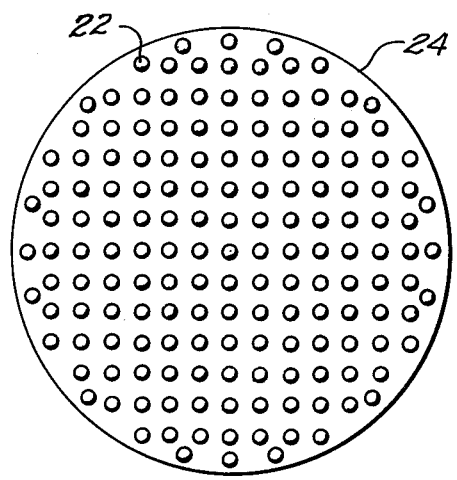
FIG. 4 shows an optional aluminum spacer for separating the balls into a less dense array.

FIG. 4 shows an optional spacer 24 in the form of a disc of aluminum which has holes in which balls 22 are positioned. This spacer is utilized in situations where a less dense array provide the desired information.

SUMMATION

Thus, it is seen that I have provided a passive stress gauge that can provide a cost-effective method of measuring peak stress in soil and on a soil-structure interface. Ideally, the deformation characteristics of a soil stress gauge should match the soil as closely as possible. However, a flat, disc-shaped gauge whose stiffness is greater than that of the soil is not very sensitive to variations in soil properties. Since pretest predictions of peak stress resulting from nuclear and high-explosive detonations are often very inaccurate, the widest possible sensing range is clearly advantageous. For maximum usefulness when dealing with pulses of different rise times and durations, the gauge should be free of rate effects over as broad a range of pulse shapes as possible.

The invention of this disclosure utilizes the principle of having a layer of small hardened steel balls between softer materials. The balls may be closely packed or separated from each other by a spacer of aluminum. Indentations in the softer materials, their diameters measured by a microscope, indicate the maximum compressive force that has been exerted at the location of each ball. The gauge body package serves to seal off the space around the balls from external pressure, and to provide protection against shear in the plane of the sandwich. In a high-ranged gauge, the balls can be closely packed, forming a plane hexagonal array except at the edge. With 3/32-inch diameter balls, such an array would have 20.305 balls per square centimeter, or about 131 per square inch. In a lower-ranged version, the balls can be separated by a 1.27 millimeter thick spacer into an array with 3.875 balls per square centimeter or about 25 per square inch. This latter version is a square array except at the edges, but the ball density there is very nearly the same as at the center.

Slight modification of the Brinell sandwich could be used to measure peak impact force. This has been done in a battle tank suspension simulator subjected to ground motion. Also, the Brinell sandwich could readily be packaged to optimize location and distribution of impact forces over a wider area. This could be useful in crash testing. And a Brinell sandwich could be used as a peak reading uniaxial accelerometer to measure peak deceleration of a projectile upon impact.

An important feature of this invention is the independence from pulse rise time and duration for a broad range of pulses, down to rise times of 0.1 millisecond and durations of 0.2 millisecond. When dealing with instruments whose operation depends on plastic deformation, it is important to keep in mind that almost all materials are to some extent strain rate sensitive. That is, generally, the plastic flow stress depends on the rate of deformation, especially at the high rates of deformation involved with short pulses. Clearly, if the indicated reading depends on pulse rise time and duration as well as on the peak value, the measurement becomes ambiguous. Knowledge of possible rate sensitivity in the particular plastic flow configuration employed in the gauge is essential. This invention utilizes the results of a laboratory investigation of dynamic ball-indentation in otherwise well-known materials to produce unambiguous results.

With the use of the aluminum alloy 7075-T6 discussed earlier, strain rate effects have not been detected. As for alloy 6061-T6, large impressions in the alloy appear to involve barely detectable rate effect. The use of one disc of 7075-T6 and one of 6061-T6 eliminates even this slight rate effect by utilizing only the 7075-T6 disc for readout.

This Brinell sandwich transducer is a dynamic transducer in that it can handle short pulses, with durations less than a millisecond, as well as static tests. This characteristic is also important in other applications such as the measurement of peak impact force or peak acceleration mentioned above.

The Brinell sandwich transducer soil stress gauge of this invention incorporates a large number of indenters and relatively flexible gauge body faces. As a result, this gauge indicates a stress distribution, instead of merely indicating the net total load on the array. This has several important practical consequences:

1. Performance of the Brinell sandwich transducer soil stress gauge is not significantly affected by friction between the gauge parts at the edge. Such edge friction arises when high pressures close radial clearances and also when external shear stress forces the gauge body faces in opposite directions. In the Brinell sandwich transducer, edge friction affects only the impressions near the edge. Pressures of interest are determined from a sample pattern of impressions at the center.

2. Performance of the Brinell sandwich transducer soil stress gauge is influenced by arching effects in the soil near the edge to a much lesser extent than in the prior art. The sensing faces deflect more under load than the solid metal edge. The soil responds to this relative movement by transferring part of the load from the edge of the sensing faces onto the solid annulus. This effect diminishes with distance away from the edge, and confining the readout to a sample pattern of impressions at the center eliminates its influence on measurements in a wide variety of earth media.

3. The Brinell sandwich transducer soil stress gauges can diagnose problems due to imperfect placement in the medium, such as a local void or inclusion of spongy grout. Locations of local voids and/or soft inclusions show up as regions of low impression sizes on the indented inserts. This capability is important in excluding misleading readings from the data.

4. The Brinell sandwich transducer soil stress gauges can also be used to indicate other anomalies in the external stress field. For example, placing these gauges very close to a buried charge of TNT produces local regions of impression sizes significantly larger than the rest on the same indented insert. These are believed to be the result of jetting of the TNT.

As various changes could be made in the above constructions and methods without departing from the scope of the invention, it is intended that all matter contained in the above description or shown in the accompanying drawings shall be interpreted as illustrative and not in a limiting sense.

What is claimed is:

1. In a Brinell sandwich stress gauge having relatively flexible gauge body faces,
    a disc-shaped bottom means,
    a tubular side means comparatively thicker than and integral with said bottom means to define therewith an open circular chamber,
    a first disc of relatively low strain rate sensitive material dimensioned to fit snugly in the bottom of said circular chamber,
    a plurality of hardened steel balls formed in a layer atop said first disc means,
    a second disc of relatively low strain rate sensitive material dimensioned to fit snugly on top of said layer of balls,
    a cover means of thickness comparable to said bottom means having sealing accommodating means therein,
    sealing means therefor, and
    a retaining ring to complete the encasement means.

2. In the Brinell sandwich stress gauge of claim 1, at least one of said discs is of aluminum alloy 7075-T6.

3. In the Brinell sandwich stress gauge of claim 1, one of said discs is of aluminum alloy 7075-T6, and the other of said discs is of aluminum alloy 6061-T6.

4. In the Brinell sandwich stress gauge of claim 1, both of said discs are of aluminum alloy 7075-T6.

5. In a Brinell sandwich stress gauge having relatively flexible gauge body faces,
    a disc-shaped bottom means,
    a tubular side means comparatively thicker than said bottom means and integral with said bottom means to define an open circular chamber,
    a first relatively thin, compared to the thickness of said bottom means, disc means of low strain rate sensitive material dimensioned to fit snugly in the bottom of said circular chamber,
    a plurality of hardened steel balls formed in a layer atop said first disc means,
    a second relatively thin disc means of low strain rate sensitive material dimensioned to fit snugly on top of said layer of balls,
    a cover means of thickness comparable to said bottom means having a groove in the upper periphery thereof and positioned above said second disc means,
    a sealing means secured in said groove in said cover means, and
    a retaining ring secured to said tubular side means and engaging said sealing means to maintain a snug fit of all of said sandwich means.

6. In the Brinell sandwich stress gauge of claim 5, said plurality of hardened steel balls are tightly packed to a maximum number of indenters for said Brinell Sandwich.

7. In the Brinell sandwich stress gauge of claim 5, a spacer means for separating said plurality of hardened steel balls and for securing said balls in a pattern.

* * * * *